(12) United States Patent
Inoue (10) Patent No.: US 12,048,588 B2
(45) Date of Patent: Jul. 30, 2024

(54) ULTRASOUND DIAGNOSTIC APPARATUS AND DIAGNOSIS ASSISTANCE METHOD

(71) Applicant: FUJIFILM Healthcare Corporation, Kashiwa (JP)

(72) Inventor: Kenta Inoue, Chiba (JP)

(73) Assignee: FUJIFILM Healthcare Corporation, Chiba (JP)

( * ) Notice: Subject to any disclaimer, the term of this patent is extended or adjusted under 35 U.S.C. 154(b) by 186 days.

(21) Appl. No.: 17/744,834

(22) Filed: May 16, 2022

(65) Prior Publication Data

US 2022/0378403 A1 Dec. 1, 2022

(30) Foreign Application Priority Data

May 25, 2021 (JP) .................. 2021-087804

(51) Int. Cl.
*A61B 8/00* (2006.01)
*A61B 8/08* (2006.01)
*A61B 8/15* (2006.01)
*G06T 7/00* (2017.01)
*G06T 7/13* (2017.01)
*G06T 7/174* (2017.01)
(Continued)

(52) U.S. Cl.
CPC ............ *A61B 8/463* (2013.01); *A61B 8/0825* (2013.01); *A61B 8/085* (2013.01); *A61B 8/15* (2013.01); *A61B 8/5207* (2013.01); *G06T 7/0012* (2013.01); *G06T 7/13* (2017.01); *G06T 7/174* (2017.01); *G06T 7/181* (2017.01); *G06T 7/62* (2017.01); *G06T 2207/10132* (2013.01); *G06T 2207/20182* (2013.01)

(58) Field of Classification Search
CPC ....... A61B 8/463; A61B 8/0825; A61B 8/085; A61B 8/15; A61B 8/5207; A61B 8/5223; A61B 8/46; A61B 8/461; A61B 8/523; G06T 7/0012; G06T 7/13; G06T 7/174; G06T 7/181; G06T 7/62; G06T 2207/10132; G06T 2207/20182; G16H 30/40; G16H 40/60
See application file for complete search history.

(56) References Cited

U.S. PATENT DOCUMENTS 5,442,462 A * 8/1995 Guissin .................. G06T 5/50
358/463
2004/0015079 A1* 1/2004 Berger .................. G01S 7/5208
600/443

(Continued)

FOREIGN PATENT DOCUMENTS

JP 2020-178989 11/2020

*Primary Examiner* — Baisakhi Roy
*Assistant Examiner* — Kaitlyn E Sebastian
(74) *Attorney, Agent, or Firm* — Paul Teng (57) ABSTRACT

An image analyzer unit performs lesion site detection for each tomographic image. In response to a lesion site detection state, the image analyzer unit outputs a position data array and a size data array that represent temporal change in position and size of the lesion site. A rate of change calculator unit calculates a rate of change that represents a degree of temporal change in tomographic image content. A smoother unit smooths the position data array and the size data array in accordance with the rate of change. A mark is generated based on the smoothed position data array and the smoothed size data array.

9 Claims, 9 Drawing Sheets

(51) Int. Cl.
*G06T 7/181* (2017.01)
*G06T 7/62* (2017.01)

(56) References Cited

U.S. PATENT DOCUMENTS

2010/0150413 A1* 6/2010 Futamura .............. G06T 7/0012
                                          382/128
2016/0117818 A1* 4/2016 Park ..................... A61B 5/7282
                                          382/131

* cited by examiner

| FRAME NUMBER (82) | DETECTION RESULT (84) | MOVEMENT SPEED (86) | SMOOTHING COUNT (88) | CENTER POINT COORDINATES (90) | SMOOTHED CENTER POINT COORDINATES (92) | UPPER-LEFT CORNER POINT COORDINATES (94) | SMOOTHED UPPER-LEFT CORNER POINT COORDINATES (96) |
|---|---|---|---|---|---|---|---|
| ... | ... | ... | ... | ... | ... | ... | ... |
| 11 | N | — | — | — | — (98) | — | — (100) |
| 12 | Y | 10 | 5 | C12 | — | L12 | — |
| 13 | Y | 11 | 5 | C13 | C13' (C12-C13) | L13 | L13' (L12-L13) |
| 14 | Y | 8 | 4 | C14 | C14' (C12-C14) | L14 | L14' (L12-L14) |
| 15 | Y | 10 | 5 | C15 | C15' (C12-C15) | L15 | L15' (L12-L15) |
| 16 | Y | 11 | 5 | C16 | C16' (C12-C16) | L16 | L16' (L12-L16) |
| 17 | Y | 10 | 5 | C17 | C17' (C13-C17) | L17 | L17' (L13-L17) |
| 18 | Y | 10 | 5 | C18 | C18' (C14-C18) | L18 | L18' (L14-L18) |
| ... | ... | ... | ... | ... | ... | ... | ... |
| 30 | N | — | — | — | — | — | — |
| 31 | Y | 30 | 3 | C31 | — | L31 | — |
| 32 | Y | 40 | 2 | C32 | C32' (C31-C32) | L32 | L32' (L31-L32) |
| 33 | Y | 50 | 1 | C33 | — | L33 | — |
| 34 | Y | 55 | 1 | C34 | — | L34 | — |
| ... | ... | ... | ... | ... | ... | ... | ... |

ULTRASOUND DIAGNOSTIC APPARATUS AND DIAGNOSIS ASSISTANCE METHOD

CROSS REFERENCE TO RELATED APPLICATION

This application claims priority to Japanese Patent Application No. 2021-087804 filed on May 25, 2021, which is incorporated herein by reference in its entirety including the specification, claims, drawings, and abstract.

TECHNICAL FIELD

The present disclosure relates to an ultrasound diagnostic apparatus and a diagnosis assistance method and, in particular, to a technique of displaying a mark on an ultrasound image, the mark providing notification of a lesion site.

BACKGROUND

Breast ultrasound inspection involves placing a probe in contact with the surface of breasts and scanning the probe along the surface of the breasts. During the scanning, an inspector observes a real-time tomographic image that is displayed on a display, and through the observation, determines whether or not there is a lesion site. If a lesion site is found, the lesion site and its surrounding tissue are inspected closely. This process is similarly applicable to ultrasound inspection of other organs.

It is not easy to visually identify a lesion site that temporarily appears on a tomographic image that changes in real time. Especially, in ultrasound inspection of breasts, as the tissue that appears on a tomographic image has a multilayered structure, it is not easy for the inspector to instantly identify a lesion site therein.

One of techniques for assisting with identification of a lesion site is computer-aided detection (CADe). This technique is directed toward detecting, for example, a lesion site (to be more precise, a lesion site candidate) within a tomographic image for each frame and, when a lesion site is included within the tomographic image, providing notification of the lesion site. For example, a mark that encloses the lesion site is displayed on the tomographic image. CADe is used together with computer-aided diagnosis (CAD) or is included in CAD.

JP 2020-178989 A ("Document 1") discloses a medical device having a CAD function. This medical device has a function of changing the color of a mark in accordance with probe scanning speed, thereby showing the probe scanning speed to the inspector. Document 1 does not disclose a technique related to smoothing of the mark. The term "lesion site" as used herein represents a site that potentially includes a disease or a site that should be examined carefully.

SUMMARY

An ultrasound diagnostic apparatus that incorporates a CADe function or a CAD function displays a mark on an ultrasound image for providing notification of a lesion site. A mark that pops up and continues to be displayed can notify the inspector of the presence of a lesion site, thereby suggesting the inspector check the lesion site closely.

However, the display of the mark may be unstable depending on the circumstances when marks are faithfully generated and displayed in accordance with individual lesion site detection results while the content of ultrasound images is almost unchanged. If the position or the size of a mark changes rapidly frame to frame, the displayed mark flickers and causes the inspector who observes the mark to feel stress or anxiety. This can be resolved by applying some smoothing processing before displaying the mark, but then a problem may arise in that the mark is not responsively displayed in response to a lesion site that has appeared instantaneously under circumstances where the content of ultrasound images is changing significantly. This may become a cause of overlooking a lesion site.

The present disclosure is directed toward enabling mark display that suits the circumstances when providing notification of a detected lesion site using a mark.

According to one aspect of the present disclosure, there is provided an ultrasound diagnostic apparatus comprising an analyzer configured to determine a location of a lesion site for each set of frame data based on a frame data array obtained by repeatedly scanning an ultrasound beam, thereby outputting a location data array; a smoother configured to smooth the location data array while dynamically changing a smoothing level in accordance with a rate of change that represents a degree of temporal change in frame data content, thereby outputting a smoothed location data array; and a generator configured to generate a mark for providing notification of the lesion site in accordance with the smoothed location data array, wherein the mark is displayed on an ultrasound image that is formed based on the frame data array.

According to another aspect of the present disclosure, there is provided a diagnosis assistance method comprising the steps of determining a location of a lesion site for each set of frame data based on a frame data array obtained by repeatedly scanning an ultrasound beam, thereby generating a location data array; smoothing the location data array while dynamically changing a smoothing level in accordance with a rate of change that represents a degree of temporal change in frame data content, thereby generating a smoothed location data array; and generating a mark for providing notification of the lesion site in accordance with the smoothed location data array, wherein the mark is displayed on an ultrasound image that is formed based on the frame data array.

According to still another aspect of the present disclosure, there is provided a non-transitory storage medium storing a program for performing a diagnosis assistance method in an information processing apparatus, the program comprising the functions of determining a location of a lesion site for each set of frame data based on a frame data array obtained by repeatedly scanning an ultrasound beam, thereby generating a location data array; smoothing the location data array while dynamically changing a smoothing level in accordance with a rate of change that represents a degree of temporal change in frame data content, thereby generating a smoothed location data array; and generating a mark for providing notification of the lesion site in accordance with the smoothed location data array, wherein the mark is displayed on an ultrasound image that is formed based on the frame data array.

BRIEF DESCRIPTION OF DRAWINGS

Embodiments of the present disclosure will be described based on the following figures, wherein.

DESCRIPTION OF EMBODIMENTS

Embodiments of the present disclosure will be described below with reference to the accompanying drawings.

(1) Overview of Embodiments

An ultrasound diagnostic apparatus according to an embodiment of the present disclosure includes an analyzer unit, a smoother unit, and a generator unit. The analyzer unit determines the location of a lesion site for each set of frame data based on a frame data array obtained by repeatedly scanning an ultrasound beam, thereby outputting a location data array. The smoother unit smooths the location data array while dynamically changing the smoothing level in accordance with a rate of change that represents a degree of temporal change in frame data content, thereby outputting a smoothed location data array. The generator unit generates a mark for providing notification of the lesion site in accordance with the smoothed location data array. The mark is displayed on an ultrasound image that is formed based on the frame data array. The analyzer unit corresponds to the analyzer. The smoother unit corresponds to the smoother. The generator unit corresponds to the generator.

With the above-described structure, the mark is displayed in accordance with the smoothed location data array. In this process, the smoothing level is set in accordance with a rate of change that represents a degree of temporal change in frame data content. When the rate of change is low, or, in other words, when the content of ultrasound images is not changing significantly, unstable mark display can be prevented or mitigated by increasing the smoothing level. For example, a flickering phenomenon of the displayed mark can be reduced. On the other hand, when the rate of change is high, or, in other words, when the content of ultrasound images is changing significantly, the mark can be responsively displayed by decreasing the smoothing level, so that overlooking a lesion site that appears instantaneously can be prevented or mitigated. A structure according to an embodiment of the present disclosure can achieve mark display that suits the circumstances, and can therefore increase the reliability of the mark display.

The location of a lesion site represents an area or a site where a lesion site is present in an ultrasound image. A plurality of points representative of a lesion site may be identified as the location of a lesion site, or a region where there is a lesion site or a region that includes a lesion site may be identified as the location of a lesion site. For example, probe movement information, frame data difference information, or a transmission and reception frame rate may be referred to either as the rate of change, or for use in calculating the rate of change.

In an embodiment of the present disclosure, the analyzer unit determines the position and size of the lesion site as the location of the lesion site and outputs a position data array and a size data array as the location data array. The smoother unit includes a first smoother unit that smooths the position data array and a second smoother unit that smooths the size data array. The generator unit generates a mark in accordance with the smoothed position data array and the smoothed size data array. In an embodiment of the present disclosure, each set of position data of the position data array represents a center position of a region that includes a lesion site, and each set of size data of the size data array represents a corner position of the region. The first smoother unit corresponds to the first smoother. The second smoother unit corresponds to the second smoother.

Causes of unstable mark display include temporal fluctuations in the position detected in connection with a lesion site and temporal fluctuations in the size detected in connection with a lesion site. These are smoothed individually. As a result, the whole mark can be displayed stably under circumstances where the content of ultrasound images is not changing significantly. In a modification example, the mark itself may be smoothed.

In an embodiment of the present disclosure, the smoother unit decreases the smoothing level in accordance with an increase in the rate of change. With this structure, the importance of responsivity increases as the degree of change in frame data content increases, and the importance of smoothness or stability increases as the degree of change in frame data content decreases.

In an embodiment of the present disclosure, the smoother increases the smoothing level by increasing a frame data count, which is the number of sets of frame data used in smoothing, and the smoother decreases the smoothing level by decreasing the frame data count. A weighting function may be used for smoothing. A value representing the smoothing level or the number of frames used in smoothing may be displayed on a screen. There may be provided a mode of fixing the smoothing level at a predetermined value either as selected by the user, or automatically.

In an embodiment of the present disclosure, the smoother unit determines whether or not there is temporal discontinuity of the lesion site based on an output from the analyzer unit and limits the generation of a mark in response to determination of the temporal discontinuity. In an embodiment of the present disclosure, the smoother unit determines whether or not there is spatial discontinuity of the lesion site based on an output from the analyzer unit and limits the generation of a mark in response to determination of the spatial discontinuity. In response to determination of the temporal discontinuity or the spatial discontinuity, a mark may be hidden from view by limiting the generation of a mark, or the display of a mark for which smoothing is performed may be limited. The determination that a temporal continuity condition is not satisfied, which will be described later, corresponds to the determination of the temporal discontinuity. The determination that a spatial continuity condition is not satisfied, which will be described later, corresponds to the determination of the spatial discontinuity.

A diagnosis assistance method according to an embodiment of the present disclosure includes an analyzing step, a smoothing step, and a generating step. The analyzing step comprises determining a location of a lesion site for each set of frame data based on a frame data array obtained by repeatedly scanning an ultrasound beam, thereby generating a location data array. The smoothing step comprises smoothing the location data array while dynamically changing a smoothing level in accordance with a rate of change that represents a degree of temporal change in frame data content, thereby generating a smoothed location data array. The generating step comprises generating a mark for providing notification of the lesion site in accordance with the smoothed location data array. The mark is displayed on an ultrasound image that is formed based on the frame data array.

The above-described diagnosis assistance method may be implemented through a function of hardware or through a function of software. In the latter case, a program for performing the diagnosis assistance method is installed on an information processing apparatus via a portable storage medium or over a network. The concept of the information processing apparatus encompasses ultrasound diagnostic apparatuses, ultrasound image processing apparatuses, and computers. The information processing apparatus includes a non-transitory storage medium having the above-described program stored therein.

(2) Details of Embodiments

Figure 1:
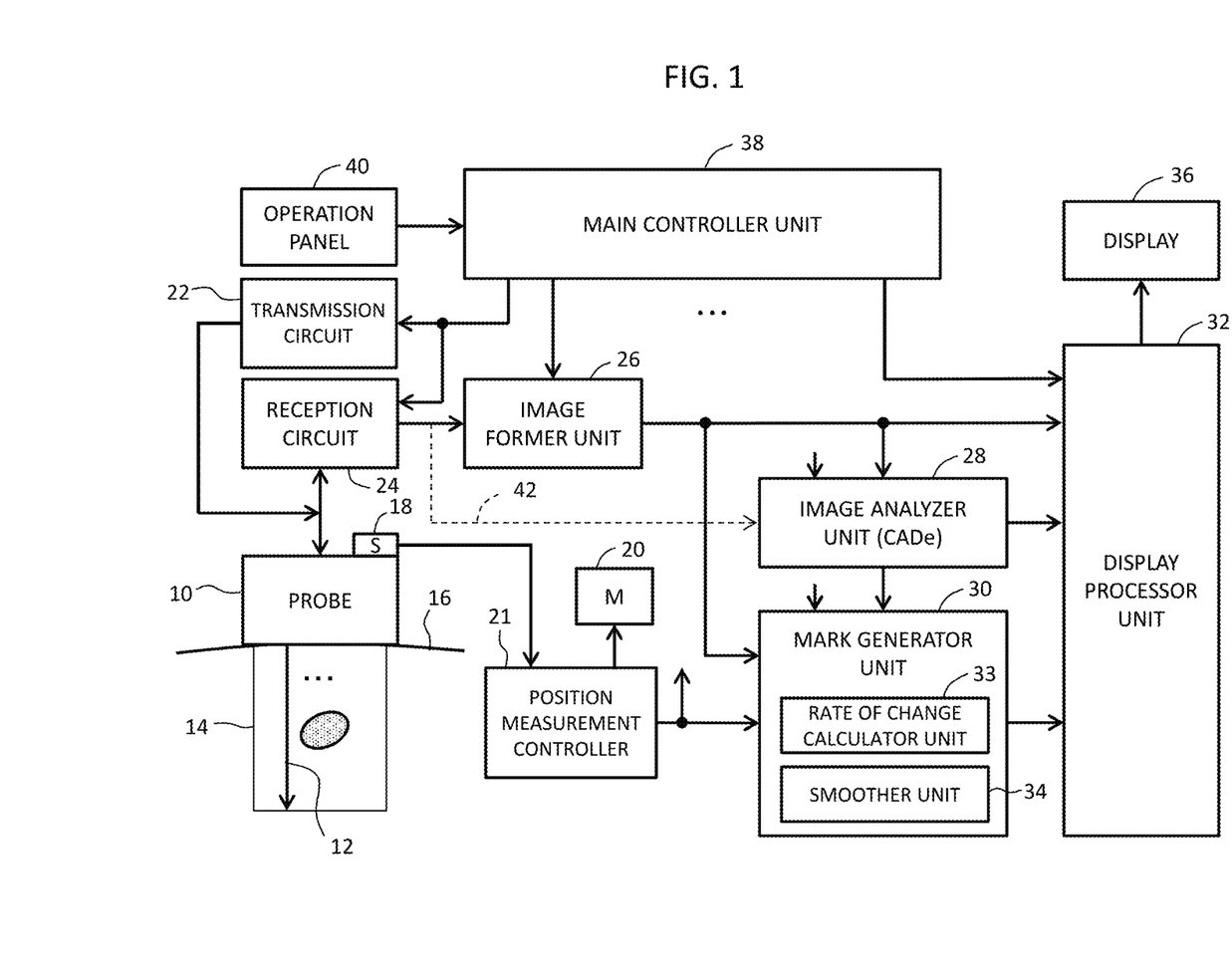
FIG. 1 is a block diagram illustrating an ultrasound diagnostic apparatus according to an embodiment of the present disclosure.

FIG. 1 illustrates a structure of an ultrasound diagnostic apparatus according to an embodiment of the present disclosure in the form of a block diagram. The ultrasound diagnostic apparatus is a medical apparatus that is placed in a healthcare facility such as a hospital and which forms an ultrasound image based on reception signals obtained through transmission and reception of ultrasound waves to and from a living body (subject). In an embodiment of the present disclosure, ultrasound diagnosis target organs are, for example, breasts.

In breast mass screening, a lesion site should be identified quickly and without being overlooked. To assist an inspector with identifying a lesion site, an ultrasound diagnostic apparatus according to an embodiment of the present disclosure has a CADe function of automatically detecting a lesion site (for example, a low-luminance tumor image) included in an ultrasound image. This will be described in detail later.

A probe 10 serves as means for transmitting and receiving ultrasound waves. The probe 10 is a portable transmitter receiver, which is held and operated by an inspector (such as a physician or a clinical examination technician). For breast ultrasound diagnosis, the wave transmission and reception surface (specifically, the surface of an acoustic lens) of the probe 10 is placed in contact with the surface 16 of the chest of the subject. The probe 10 is scanned manually along the surface 16 of the chest while a tomographic image that is displayed in real time is being observed.

In the illustrated example structure, the probe 10 includes a transducer array that consists of a plurality of transducers that are arrayed one-dimensionally. An ultrasound beam (transmission beam and reception beam) 12 is formed by the transducer array, and a scanning plane 14 is formed by electronically scanning the ultrasound beam 12. The scanning plane 14 is an observation plane; that is, a two-dimensional data acquiring region. Examples of known methods of electronically scanning the ultrasound beam 12 include an electronic sector scanning method and an electronic linear scanning method. Convex scanning of the ultrasound beam 12 may also be performed. A 2D transducer array may also be provided in the ultrasound probe 10 to obtain volume data from a living body by two-dimensionally scanning the ultrasound beam. A reception frame data array, which will be described later, is generated through repetition of scanning of the ultrasound beam.

The illustrated example structure includes a position measurement system for obtaining position information of the probe 10. The position measurement system includes a magnetic sensor 18, a magnetic field generator 20, and a position measurement controller 21. The magnetic sensor 18 is disposed on the probe 10 (to be more precise, on a probe head in the probe). The magnetic sensor 18 detects a magnetic field generated by the magnetic field generator 20. Three-dimensional coordinate information of the magnetic sensor 18 is obtained in this manner. The position and the orientation of the probe 10 are determined based on the three-dimensional coordinate information. The position information is transmitted from the position measurement controller to a mark generator unit 30 and a main controller unit 38.

A transmission circuit 22 serves as a transmission beam former. Specifically, the transmission circuit 22 supplies a plurality of transmission signals to the transducer array in parallel with each other during transmission. A transmission beam is formed in this manner. During reception, a reflected wave from inside a living body reaches the transducer array, and then a plurality of reception signals are output from the plurality of transducers in parallel with each other. A reception circuit 24 serves as a reception beam former and generates beam data through phase alignment and summing (also called delay and summing) of the plurality of reception signals.

As an aside, a plurality of sets of beam data which are successive in the electronic scanning direction are generated for a single electronic scan, and they constitute reception frame data corresponding to the scanning plane 14. Each set of beam data is composed of a plurality of sets of echo data which are successive in the depth direction. A beam data processor unit is provided downstream of the reception circuit 24, but is not illustrated in the drawings.

An image former unit 26 is an electronic circuit that generates a tomographic image (B-mode tomographic image) based on the reception frame data. This includes a digital scan converter (DSC). The DSC has, for example, a coordinate conversion function, a pixel interpolation function, and a frame rate conversion function. More specifically, the image former unit 26 forms a display frame data array based on the reception frame data array. A plurality of sets of display frame data that constitute the display frame data array are a plurality of sets of tomographic image data, and a real-time video image is constructed from those sets of data. Ultrasound images other than tomographic images may also be generated. For example, a color flow mapping image may be formed, or a three-dimensional image that stereoscopically represents a tissue may be formed. The display frame data array is transmitted to an image analyzer unit 28 and a display processor unit 32.

The image analyzer unit 28 is a module that performs a CADe function. The image analyzer unit 28 executes lesion site detection processing for each set of display frame data, or, in other words, for each tomographic image. Specifically, a machine learning network such as a convolutional neural network (CNN) is used to search a tomographic image for a region having a feature that is similar to any previously learned lesion site feature. A detection target lesion site is determined beforehand by a network designer. Examples of the detection target lesion site include a mass lesion site and a non-mass lesion site. During the lesion site detection processing, processing such as binarization processing or edge detection processing may be applied to the tomographic image.

In response to detection of a lesion site, lesion site information is output from the image analyzer unit 28. The lesion site information includes a lesion site detection flag, a confidence level of the lesion site, position information (position data) of the lesion site, and size information (size data) of the lesion site. For each set of display frame data, lesion site information is transmitted from the image analyzer unit 28 to the mark generator unit 30. In other words, the position data array and the size data array are transmitted from the image analyzer unit 28 to the mark generator unit 30.

The position information of a lesion site is, for example, information representing coordinates of a center point (or center of gravity point) of a closed region corresponding to the lesion site or information representing coordinates of a center point (or center of gravity point) of a shape enclosing the lesion site. The size information of a lesion site is, for example, information representing a size of a shape enclosing the lesion site. For example, a rectangle circumscribing a lesion site and enclosing the lesion site may be defined to determine the size of the lesion site from the coordinates of the center point of the rectangle and the coordinates of the upper-left corner point of the rectangle. Under the precondition that the coordinates of the center point are determined, the coordinates of the upper-left corner point may be considered the size information of the lesion site. As the size information of a lesion site, the area of a closed region corresponding to the lesion site may be determined. A plurality of lesion sites may be detected in parallel with each other. The position information and the size information of a lesion site may be collectively referred to as location information of the lesion site.

For each set of display frame data, the mark generator unit 30 generates a mark based on the lesion site information. The mark is a display element that represents an area where a lesion site is present. Specifically, the mark takes the form in which it encloses the lesion site, and the center position and size of the lesion site may be determined through observation of the mark. In continuous observation of the mark on a time axis, the mark corresponds to a dynamic shape (video image). In individual observation of the mark for each set of display frame data, the mark corresponds to a static shape (still-frame image).

According to an embodiment of the present disclosure, the mark generator unit 30 includes a rate of change calculator unit 33 and a smoother unit 34. For each set of display frame data, the rate of change calculator unit 33 calculates a rate of change as information representing a degree of temporal change in display frame data content. For example, a difference or correlation value between two sets of display frame data may be calculated to use the result of the calculation as the rate of change. The rate of change may be calculated based on the temporal change in the position information output from the position measurement system. The reason is that the temporal change in display frame data content is assumed to be large when the amount of probe movement (probe movement speed) is large and that the temporal change in display frame data content is assumed to be small when the amount of probe movement is small. The rate of change may be calculated based on a plurality of items of information representing a degree of temporal change in display frame data content.

To calculate a correlation value between two sets of display frame data, reference areas may be set for individual sets of display frame data based on the center position of a lesion site, so that a correlation value between two reference areas can be calculated. In that case, a correlation value may be calculated by calculating a difference in pixel value for each set of coordinates and standardizing the total sum of those differences by the number of pixels (area). The rate of change may be calculated based on, for example, a histogram correlation value between two reference areas or an optical flow calculated between two reference areas. Prior to the calculation of the rate of change, preprocessing such as segmentation or binarization processing may be applied to respective sets of display frame data.

The rate of change may be calculated based on the transmission and reception frame rate, or the transmission and reception frame rate itself may be used as the rate of change. The reason is that the temporal change in display frame data content is typically large when the transmission and reception frame rate is high, and, on the other hand, the temporal change in display frame data content is typically small when the transmission and reception frame rate is low. It can readily be understood that, when the probe 10 is standing perfectly still, the display frame data content is stable regardless of the transmission and reception frame rate. As such, the transmission and reception frame rate should be used as auxiliary information.

The smoother unit 34 executes smoothing processing. In an embodiment of the present disclosure, smoothing processing is individually applied to the position data array and the size data array generated and output by the image analyzer unit 28. In an embodiment of the present disclosure, smoothing processing is applied to the center coordinates and the upper-left corner coordinates of a rectangular region circumscribing a lesion site, as will be described later using a specific example.

The smoother unit 34 raises the smoothing level with decrease in the rate of change, and, on the other hand, lowers the smoothing level with increase in the rate of change. Adaptively varying the smoothing level in this manner makes it possible to achieve both of stable mark display under circumstances where the content of ultrasound images is not changing significantly and responsive mark display under circumstances where the content of ultrasound images is changing significantly.

In a practical application, the smoother unit 34 increases reference data count (smoothing count) in smoothing processing when the rate of change is low, and decreases reference data count in smoothing processing when the rate of change is high. The term "data count" as used herein represents the number of frames, which corresponds to a time window serving as a certain period of time from the present back to the past. The maximum and minimum reference frame count values may be determined either by the user or automatically.

Based on the smoothed position data array and the smoothed size data array, the mark generator unit 30 generates a mark in the form of a still-frame image for each set of display frame data. The mark generator unit 30 includes a memory for storing data that is necessary for smoothing processing.

More specifically, the mark generator unit 30 generates a mark only when the temporal continuity condition and the spatial continuity condition are satisfied. The mark is hidden from view when either of the temporal continuity condition and the spatial continuity condition is not satisfied. The temporal continuity condition is satisfied when a lesion site is detected continuously across a number m (where m is an integer of 2 or greater) of sets of display frame data including current display frame data. The spatial continuity condition is satisfied when the distance between the center of a lesion site in reference display frame data and the center of a lesion site in current display frame data is within a predetermined value. The reference display frame data is, for example, display frame data that was obtained at the point in time when a lesion site was first detected under circumstances where the lesion site is being detected continuously. The immediately previous display frame data may be used as the reference display frame data.

In response to interruption of detection of a lesion site within a certain time range, the display of the mark is limited. In response to movement of a lesion site that corresponds to an unnatural jump, the display of the mark is limited. These make it possible to avoid, for example, displaying a mark under circumstances where no lesion site is detected, or suddenly displaying a mark based on erroneous detection.

It can readily be understood that, as a change in probe contact state, noise, or another factor may cause temporary interruption of detection of a lesion site, mark display conditions or mark display limiting conditions may be changed either by the inspector or automatically. In response to failure to satisfy either of the continuity conditions, instead of being hidden from view, a mark may be generated and displayed based on position data and size data that are not smoothed.

To determine the smoothing level from the rate of change, the mark generator unit 30 may use a conversion table or may use a conversion function. For smoothing processing, a weight function with a weight that changes along a time axis may be used. For each set of display frame data, the mark generator unit 30 generates graphic data including a mark, and the graphic data are transmitted to the display processor unit 32.

Each of the image former unit 26, the image analyzer unit 28, and the mark generator unit 30 may be constructed from a processor. A single processor may serve as the image former unit 26, the image analyzer unit 28, and the mark generator unit 30. A CPU, which will be described later, may serve as the image former unit 26, the image analyzer unit 28, and the mark generator unit 30.

The display processor unit 32 has, for example, a color calculator function and an image combiner function. The display processor unit 32 combines graphic data including a mark with display frame data (tomographic image), thereby generating an image that is to be displayed on a display 36. The display 36 is constructed from, for example, an LCD or an organic EL display device. The display 36 displays tomographic images serving as a video image in real time, and displays a mark as part of a graphic image. The display processor unit 32 is constructed from, for example, a processor.

The main controller unit 38 controls the operation of respective components illustrated in FIG. 1. In an embodiment of the present disclosure, the main controller unit 38 is constructed from a CPU and a program. An operation panel 40 is connected to the main controller unit 38. The operation panel 40 is an input device, which includes, for example, a plurality of switches, a plurality of buttons, a trackball, and a keyboard. In an embodiment of the present disclosure, a display frame data array is supplied to the image analyzer unit 28, but a reception frame data array may be supplied to the image analyzer unit 28 (see reference numeral 42). In that case, there may be provided a second image former unit that simply generates a display frame data array from the reception frame data array.

Figure 2:
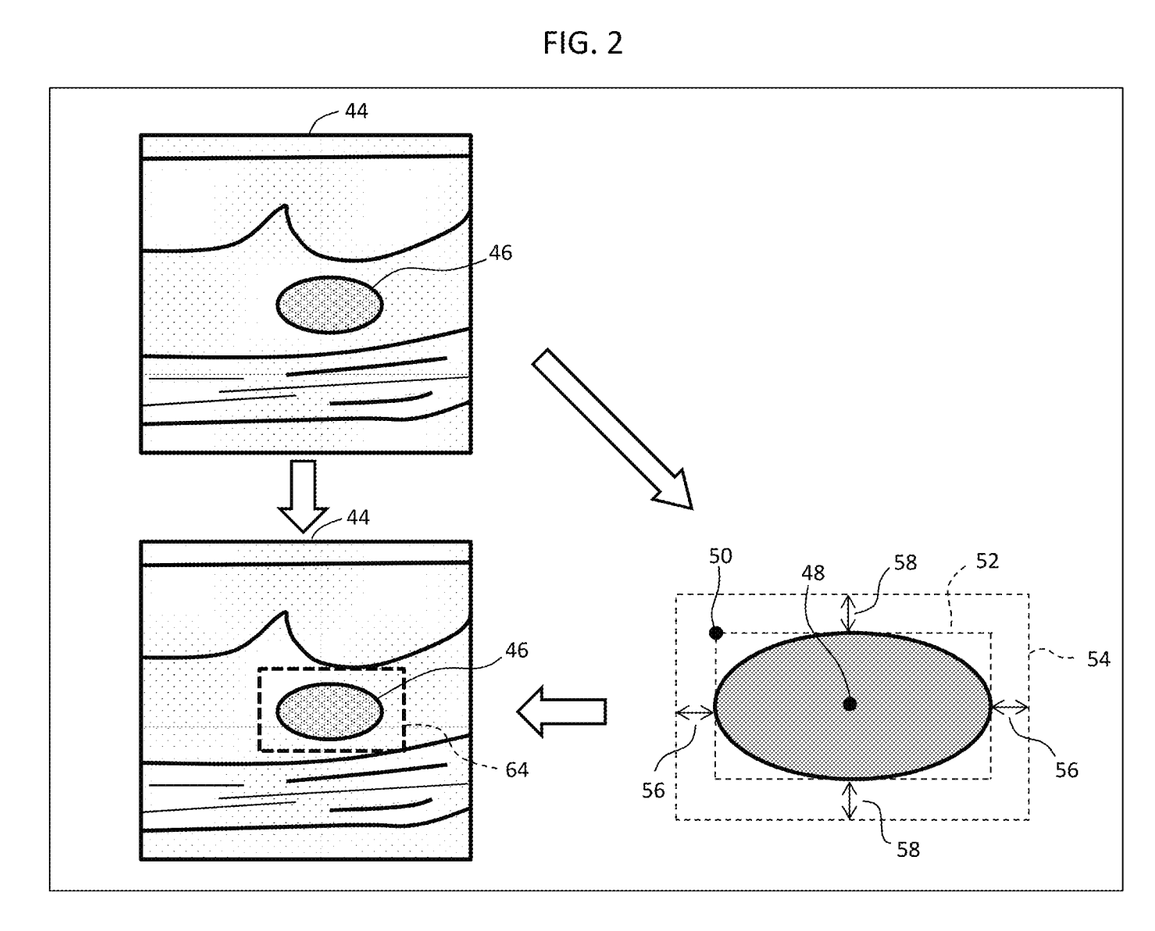
FIG. 2 illustrates mark display processing.

FIG. 2 illustrates mark display processing. A tomographic image 44 includes a lesion site 46. The lesion site 46 is detected by the image analyzer unit. During detection of the lesion site 46, for example, a rectangle (or region) 52 circumscribing the lesion site 46 is defined. In a practical application, the coordinates of a center point 48 of the rectangle 52 and the coordinates of an upper-left corner point 50 of the rectangle 52 are determined. A lesion site may be detected based on image feature extraction such as edge detection.

Outside the rectangle 52, a rectangle 54 is defined as a shape having certain margins 56 and 58 in the horizontal direction and in the vertical direction. The rectangle 54 is displayed on the tomographic image in the form of a marker 64. The marker 64 is a shape enclosing the lesion site 46 and its surroundings. In the illustrated example, the marker 64 is formed by broken lines. The manner in which the marker 64 is displayed may be freely chosen. For example, a marker formed by solid lines may be displayed, or a marker composed of four elements representing only four corner portions may be displayed. A circle or ellipse marker may be displayed.

If, while the display frame data content is almost unchanged; that is, while the lesion site is almost unchanged, the position or the size of the displayed marker 64 changes rapidly frame to frame, the inspector will experience stress or anxiety. On the other hand, it is also important to effectively prevent a lesion site that suddenly pops up from being overlooked under circumstances where the display frame data content is changing significantly. In view of the above, in an embodiment of the present disclosure, as already described above, and as will be described below by giving a specific example, adaptive smoothing processing is executed based on the rate of change.

Figure 3:
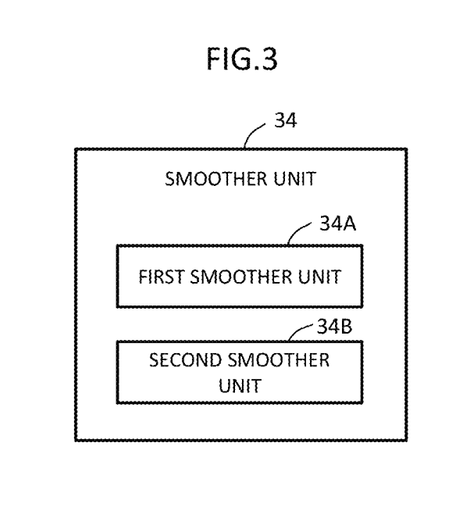
FIG. 3 illustrates an example structure of a smoother unit.

FIG. 3 illustrates a structure of the smoother unit 34. The smoother unit 34 includes a first smoother unit 34A and a second smoother unit 34B. The first smoother unit 34A smooths the position data array. The second smoother unit 34B smooths the size data array. Additionally, there may be provided a third smoother unit that smooths the confidence level of lesion site detection.

Figure 4:
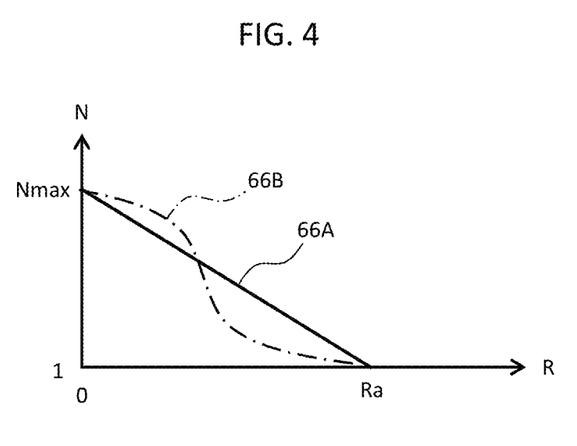
FIG. 4 illustrates a relationship between a rate of change and a smoothing count.

FIG. 4 illustrates a relationship between a rate of change R and reference data count (smoothing count) N in connection with smoothing processing. As shown by a linear function 66A, the reference data count N may be decreased monotonously with an increase in the rate of change R. The reference data count N may be determined from the rate of change R in accordance with a non-linear function 66B.

Figure 5:
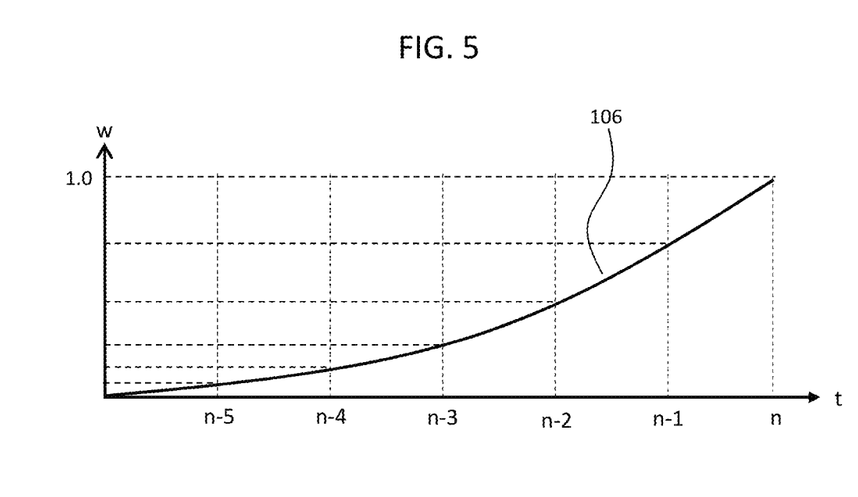
FIG. 5 illustrates an example of a weight function.

FIG. 5 illustrates a weight function 106. The horizontal axis is a time axis, wherein n represents a current frame number, and n−1 to n−5 represent past frames. The vertical axis represents a weight w. As shown by the weight function 106, more weight w may be given to newer data. The weight function 106 may be expanded and contracted to suit the time window determined from the rate of change R. A weight may be set across the board within the time window, or the weight may be changed linearly within the time window.

Figure 6:
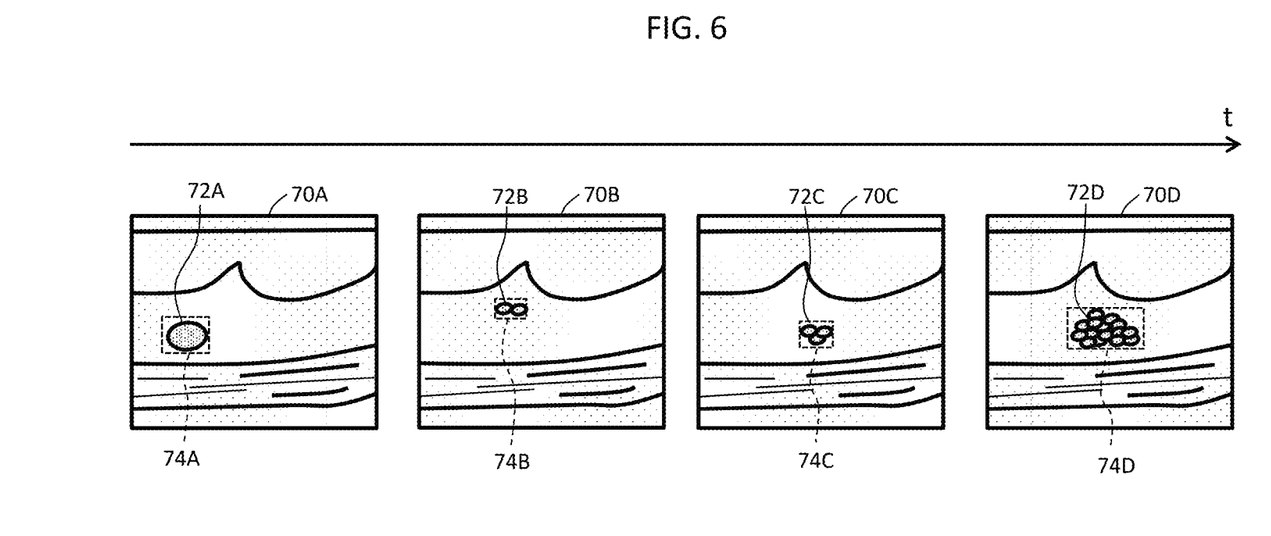
FIG. 6 illustrates a first display example.
Figure 7:
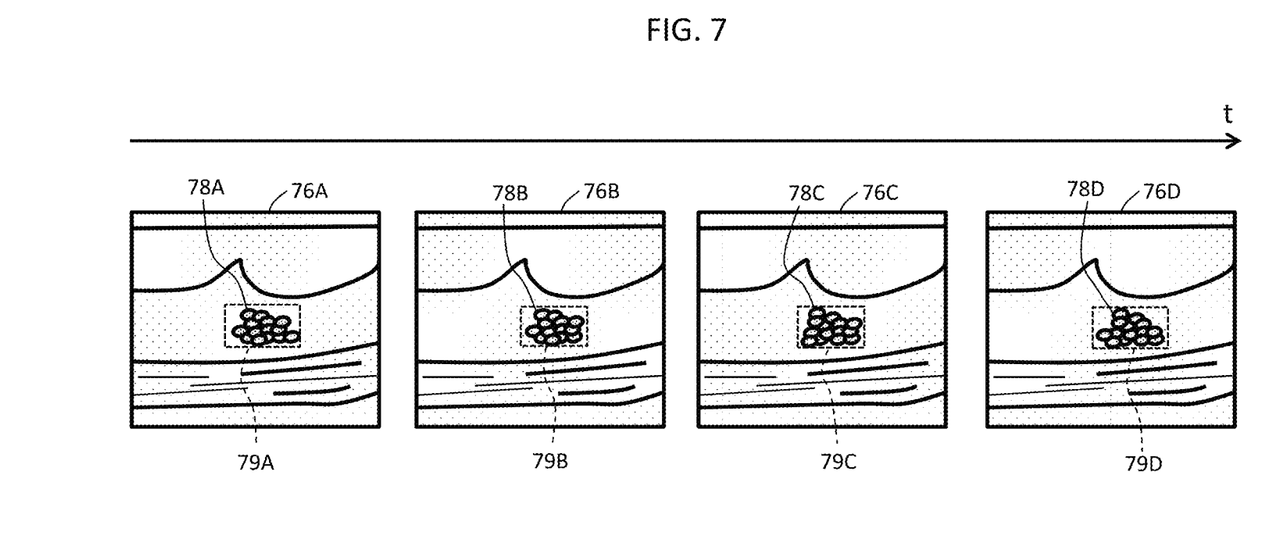
FIG. 7 illustrates a second display example.

FIG. 6 shows a first mark display example, and FIG. 7 shows a second mark display example. The first display example shows a state in which, for example, the probe movement speed is high, and a high rate of change is calculated. The second display example shows a state in which, for example, the probe movement speed is low, and a low rate of change is calculated. In FIGS. 6 and 7, the horizontal axis is a time axis.

The first mark display example illustrated in FIG. 6 includes tomographic images 70A to 70D obtained at respective times, and they include lesion sites 72A to 72D. The manner in which a lesion site appears (such as content and position) is temporally changing significantly on the time axis. In such cases, a low smoothing level is set, and marks 74A to 74D enclosing the lesion sites 72A to 72D are responsively generated and displayed at respective times. As a result, overlooking of a lesion site can be prevented or mitigated.

The second display example illustrated in FIG. 7 includes tomographic images 76A to 76D obtained at respective times, and they include lesion sites 78A to 78D. The manner in which a lesion site appears does not change significantly on the time axis. In such cases, a high smoothing level is set, and marks 79A to 79D enclosing the lesion sites 78A to 78D are suppressed from changing at respective times. As a result, a flickering phenomenon of the displayed mark is inhibited.

Figure 8:
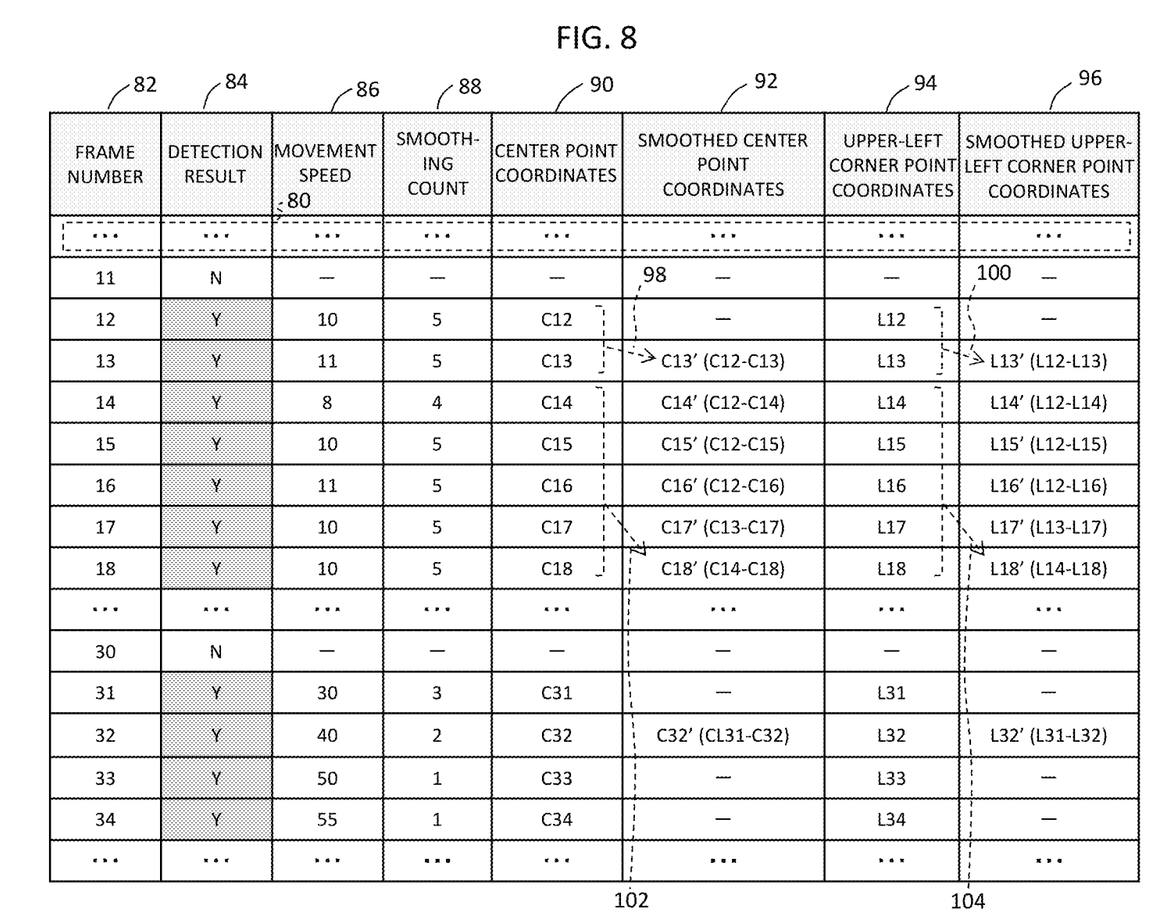
FIG. 8 illustrates an example of smoothing processing.

FIG. 8 shows a smoothing processing example. The vertical axis is a time axis. Reference numeral 80 denotes one data set. A plurality of data sets are successive along the time axis. Along the horizontal axis, there are listed a frame number 82, a lesion site detection result 84, probe movement speed 86 serving as a rate of change, smoothing count (reference data count) 88, center point coordinates 90, smoothed center point coordinates 92, upper-left corner point coordinates 94, and smoothed upper-left corner point coordinates 96.

At the point in time identified by frame number 11, no lesion site is detected. The smoothing processing is not executed. At the point in time identified by frame number 12, a lesion site is detected. While a smoothing count of 5 is determined from a movement speed of 10, smoothing is not performed at that point in time, and a mark is generated based on center point coordinates C12 and upper-left corner point coordinates L12. At the point in time identified by frame number 13, a lesion site is detected, and a smoothing count of 5 is determined from a movement speed of 11. At that point in time, smoothed center point coordinates C13' are calculated based on two sets of center point coordinates C12 and C13 (see reference numeral 98; the two sets of coordinates in parentheses represent a smoothing range). Similarly, smoothed upper-left corner point coordinates L13' are calculated based on two sets of upper-left corner point coordinates L12 and L13 (see reference numeral 100). A mark is generated based on the smoothed center point coordinates C13' and the smoothed upper-left corner point coordinates L13'.

At the point in time identified by frame number 18, a lesion site is detected (continuously detected throughout frame numbers 12 to 18), and smoothed center point coordinates C18' are calculated based on five sets of center point coordinates C14 to C18 (see reference numeral 102). Similarly, smoothed upper-left corner point coordinates L18' are calculated based on five sets of upper-left corner point coordinates L14 to L18. A mark is generated based on the smoothed center point coordinates C18' and the smoothed upper-left corner point coordinates L18' (see reference numeral 104).

While a lesion site is detected continuously from the point in time identified by frame number 31 to the point in time identified by frame number 34, the movement speed in that period of time is relatively high, and the smoothing count in that period of time is low. In an embodiment of the present disclosure, the smoothing level is adaptively determined in this manner in accordance with fluctuations in the rate of change. This includes adaptively switching the smoothing on or off.

Figure 9:
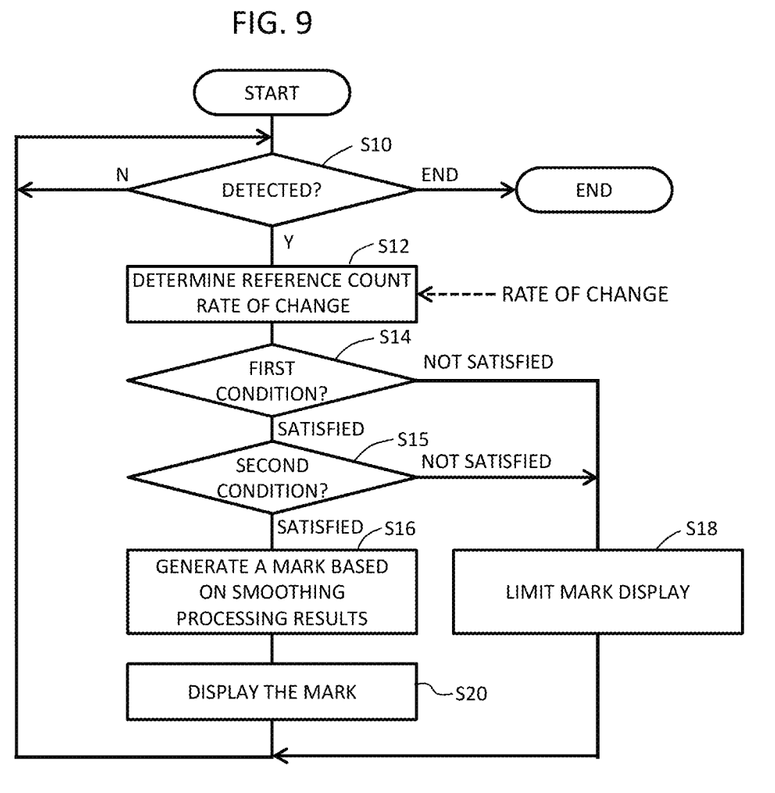
FIG. 9 is a flowchart illustrating a first operation example.

FIG. 9 shows a first operation example of the mark generator unit. In S10, a determination is made as to whether or not a lesion site is detected. The detection of a lesion site may be determined when, for example, the confidence level is greater than or equal to a predetermined value. This processing ends when an end condition in S10 is satisfied.

When it is determined that a lesion site is detected, a smoothing count (reference data count) is determined in S12 based on the rate of change. In S14, a determination is made as to whether or not the temporal continuity condition (first condition) is satisfied. In S15, a determination is made as to whether or not the spatial continuity condition (second condition) is satisfied. The process proceeds to S16 when both of the first condition and the second condition are satisfied, but to S18 when either condition is not satisfied.

In S16, a mark is generated based on results of smoothing processing; that is, based on the smoothed position data array and the smoothed size data array. In S20, the generated mark is displayed. In S18, the display of the mark is limited. Specifically, the mark is hidden from view. The foregoing processing is executed repeatedly.

Figure 10:
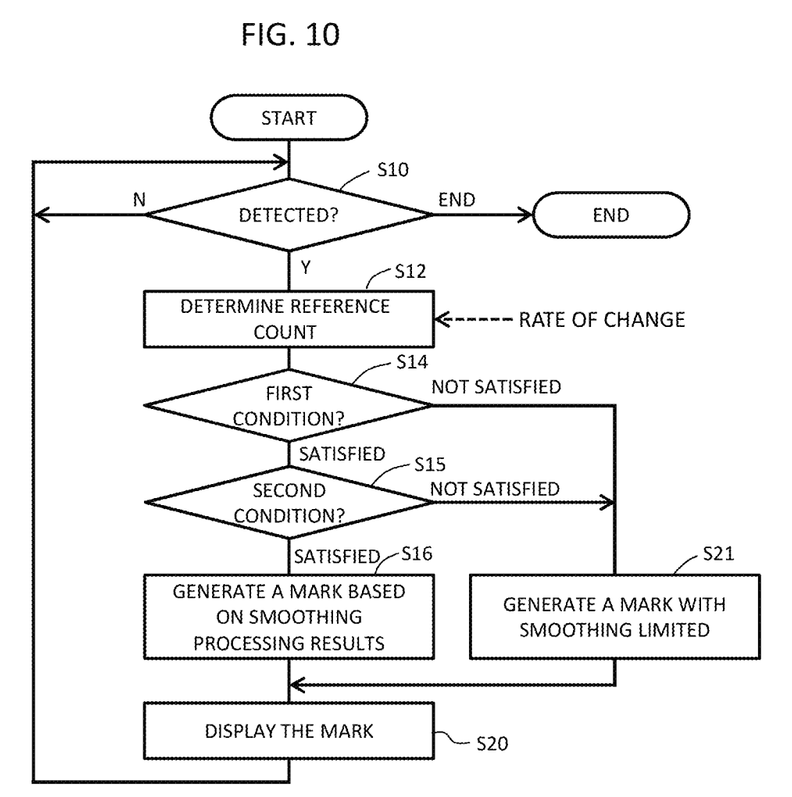
FIG. 10 is a flowchart illustrating a second operation example.

FIG. 10 shows a second operation example of the mark generator unit. In FIG. 10, the same step numbers are used for the steps similar to those in FIG. 9, and description of those steps is not repeated here.

In the second operation example, when either of the first condition and the second condition is not satisfied, the process proceeds to S21 in which a mark is generated while the smoothing is limited. In other words, a mark is generated based on the position data and the size data that are not smoothed, and it is displayed in S20.

In either of the first operation example and the second operation example, when certain conditions are satisfied, a smoothed mark is displayed in accordance with the smoothing level determined based on the rate of change. Under circumstances where the content of tomographic images is almost unchanged, occurrence of an event in which a flickering mark is displayed can be effectively prevented or mitigated. Under circumstances where the content of tomographic images is changing significantly, when a lesion site is suddenly detected, it is possible to reliably provide notification of the lesion site using a mark.

The invention claimed is:

1. An ultrasound diagnostic apparatus comprising:
    an analyzer configured to determine a location of a lesion site for each set of frame data based on a frame data array obtained by repeatedly scanning an ultrasound beam, thereby outputting a location data array;
    a smoother configured to smooth the location data array while dynamically changing a smoothing level in accordance with a rate of change that represents a content difference between two sets of frame data in the frame data array, thereby outputting a smoothed location data array, wherein the smoother decreases the smoothing level based on an increase in the rate of change; and
    a generator configured to generate a mark for providing notification of the lesion site in accordance with the smoothed location data array,
    wherein the mark is displayed on an ultrasound image that is formed based on the frame data array.

2. The ultrasound diagnostic apparatus according to claim 1,
    wherein the analyzer determines the position and size of the lesion site as the location of the lesion site and outputs a position data array and a size data array as the location data array,
    wherein the smoother includes a first smoother for smoothing the position data array and a second smoother for smoothing the size data array, and wherein the generator generates the mark in accordance with the smoothed position data array and the smoothed size data array.

3. The ultrasound diagnostic apparatus according to claim 2,
wherein each set of position data of the position data array represents a center position of a region that includes the lesion site, and
wherein each set of size data of the size data array represents a corner position of the region.

4. The ultrasound diagnostic apparatus according to claim 1, wherein the smoother decreases the smoothing level in accordance with an increase in the rate of change.

5. The ultrasound diagnostic apparatus according to claim 4, wherein
the smoother is further configured to increase the smoothing level by increasing a frame data count, which is the number of sets of frame data used in smoothing, and to decrease the smoothing level by decreasing the frame data count.

6. The ultrasound diagnostic apparatus according to claim 1, wherein the generator is configured to:
determine whether or not there is temporal discontinuity of the lesion site based on an output from the analyzer; and
hide the mark from view, in response to determination of the temporal discontinuity.

7. The ultrasound diagnostic apparatus according to claim 1, wherein the generator is configured to:
determine whether or not there is spatial discontinuity of the lesion site based on an output from the analyzer; and
hide the mark from view, in response to determination of the spatial discontinuity.

8. A diagnosis assistance method comprising the steps of:
determining a location of a lesion site for each set of frame data based on a frame data array obtained by repeatedly scanning an ultrasound beam, thereby generating a location data array;
smoothing the location data array while dynamically changing a smoothing level in accordance with a rate of change that represents a content difference between two sets of frame data in the frame data array, thereby generating a smoothed location data array, the smoothing level being decreased based on an increase in the rate of change; and
generating a mark for providing notification of the lesion site in accordance with the smoothed location data array, and displaying the mark on an ultrasound image that is formed based on the frame data array.

9. A non-transitory storage medium storing a program for performing a diagnosis assistance method in an information processing apparatus, the program comprising the functions of:
determining a location of a lesion site for each set of frame data based on a frame data array obtained by repeatedly scanning an ultrasound beam, thereby generating a location data array;
smoothing the location data array while dynamically changing a smoothing level in accordance with a rate of change that represents a content difference between two sets of frame data in the frame data array, thereby generating a smoothed location data array, the smoothing level being decreased based on an increase in the rate of change; and
generating a mark for providing notification of the lesion site in accordance with the smoothed location data array, and displaying the mark on an ultrasound image that is formed based on the frame data array.

* * * * *